(12) United States Patent
Shalaby

(10) Patent No.: US 6,197,320 B1
(45) Date of Patent: *Mar. 6, 2001

(54) ABSORBABLE E-CAPROLACTONE POLYMERS AND MEDICAL DEVICES

(76) Inventor: Shalaby W. Shalaby, 6309 Hwy. 187, Anderson, SC (US) 29625

( * ) Notice: Subject to any disclaimer, the term of this patent is extended or adjusted under 35 U.S.C. 154(b) by 0 days.

This patent is subject to a terminal disclaimer.

(21) Appl. No.: 09/103,142

(22) Filed: Jun. 29, 1998

Related U.S. Application Data

(63) Continuation-in-part of application No. 08/660,089, filed on Jun. 3, 1996, now Pat. No. 5,773,563, which is a continuation-in-part of application No. 08/212,174, filed on Mar. 11, 1994, now Pat. No. 5,522,842.

(51) Int. Cl.⁷ ................................................... A01N 25/34
(52) U.S. Cl. .......................... 424/408; 606/230; 606/231
(58) Field of Search ............................. 424/408; 606/230, 606/231

(56) References Cited

U.S. PATENT DOCUMENTS

| | | | |
|---|---|---|---|
| 5,522,842 | * 6/1996 | Shalaby | 606/230 |
| 5,773,563 | * 6/1998 | Shalaby | 528/354 |

* cited by examiner

*Primary Examiner*—S. Mark Clardy
*Assistant Examiner*—Michael A. Williamson

(57) ABSTRACT

Crystalline, low melting -Caprolactone polymers which undergo accelerated hydrolysis, and their use as lubricant coatings and/or as coatings containing bioactive agents, as carriers of viable cells, and as coatings for open-cell microporous template or constucts for tissue regeneration; the polymers bearing basic functionalities can be linked ionically or covalently to the ester chain which induces autocatalyzed hydrolysis.

4 Claims, No Drawings

ABSORBABLE E-CAPROLACTONE POLYMERS AND MEDICAL DEVICES

This application is a Continuation-in-Part of U.S. Ser. No.08/660,089, filed Jun. 3, 1996, now U.S. Pat. No. 5,773,563, which is a Continuation-in-Part of U.S. Ser. No. 08/212,174, filed Mar. 11, 1994, now U.S. Pat. No. 5,522,842

BACKGROUND OF THE INVENTION

This invention relates to crystalline, low melting, ε-caprolactone polymers bearing basic amine functionalities which are linked to the ester chain ionically or covalently to induce catalyzed hydrolysis. The ester components can be derived from ε-caprolactone with or without small amounts of glycolide, and/or similar lactones. Such polymers with accelerated absorption profiles are especially adapted for use as transient coatings for absorbable multifilament surgical sutures (and other medical implants).

Multifilament surgical sutures such as Dexon® polyglycolide multifilament suture typically require a surface coating to improve their handling and knotting characteristics. Capitalizing on the desirable low melting temperature, crystallinity, and rheological properties of polycaprolactone and its copolymers as coating materials, several compositions based on this polymer were investigated as coatings for surgical sutures. Recognizing the fact that the ε-caprolactone homopolymer is essentially non-absorbable led to the development of copolymers of ε-caprolactone with variable amounts of more absorbable monomers to improve the coating absorbability. U.S. Pat. No. 4,624,256 discloses a suture coating copolymer of at least 90 percent ε-caprolactone and a biodegradable monomer and optionally a lubricating agent. Examples of monomers for the biodegradable polymers disclosed include glycolic acid and glycolide, as well as well-known monomers typically used to prepare absorbable polymer fibers or coatings for multifilament sutures. U.S. Pat. No. 4,788,979 and U.S. Pat. No. 4,791,929 disclose a bioabsorbable coating of a copolymer of at least 50 percent ε-caprolactone and glycolide. Sutures coated with such polymers are reported to be less stiff than sutures coated with other materials and the physical properties of the coated suture are also reported to be acceptable. U.S. Pat. No. 4,994,074 discloses copolymers of a predominant amount of ε-caprolactone, the balance being glycolide and glycolic acid. The use of glycolic acid as a comonomer into the copolymers of this invention was reported to increase the rate of absorption of the copolymer when used as a coating for multifilament surgical sutures.

Unfortunately, the problem of adequate bioabsorbability of ε-caprolactone-based polymers without detrimental effects on their desirable properties as coatings still remains. Specifically, the use of sufficient amounts of glycolide to achieve sufficient absorbability of the copolymeric coating can compromise its crystallinity and melting characteristics, for it may become amorphous or liquid near room temperature. On the other hand, the strategy of using glycolic acid to achieve the reported results in coating absorbability does limit the ability to produce sufficiently long chain molecules to achieve optimum frictional properties, due to glycolic acid's known properties as both a ring-opening initiator chain terminator. Thus, a totally new approach to modifying the absorbability of polycaprolactone and its copolymers without affecting their desirable properties as suture coatings (or coatings for surgical device) would be a more desirable goal.

SUMMARY OF THE INVENTION

One aspect of the invention are low melting, crystalline, basic nitrogenous polyesters, or polyesteramides, where the amine functionality represents between 1 and 20 percent of the total weight, while the repeat units of the polyester chain originate predominantly from ε-caprolactone. The balance ester sequences can be derived from glycolide, lactide p-dioxanone and/or one or more of the corresponding hydroxy acids. The amine functionality can be linked to the polyester chain ionically or covalently.

In another aspect, the invention is a coating for a surgical suture which displays autocatalyzed hydrolysis and improved absorbability over polyester coatings of the prior art which are devoid of any basic amine functionality. This coating comprises a low viscosity melt or a solution in an organic solvent, of the amine-bearing polyesters described above. Surprisingly, the incorporation of 1 to 10 percent of the amine functionality increased the polyester absorbability substantially, without compromising its desirable physical properties such as those associated with crystallinity and melting profile.

Polyesters bearing the amine-functionalities subject of this invention and coating derived therefrom can be used for coating bioabsorbable multifilament surgical sutures, as well as other surgical closure devices and indwelling devices. In addition, they may be used alone or as carriers or matrices for viable cells and vaccines, or as a coating containing bioactive agents such as growth factors, antimicrobials and antibiotics.

DETAILED DESCRIPTION OF THE INVENTION

Polyesters comprising predominantly ε-caprolactone polymer sequences generally refers to polymers with ε-caprolactone-based sequences of greater than 80 mole percent, the monomer compositions from which the polymers of this invention are derived. ε-Caprolactone is the predominant component of the polyester because of its low melting, exceptionally low glass transition temperature (Tg) and its ability to enhance the surface physical properties of coated multifilament sutures. Preferably, the amount of ε-caprolactone used in the synthesis of the polyester ranges from 90 to 99, more preferably 96 to 99 mole percent. For copolyesters of this invention, the remaining comonomers are preferably glycolide and/or glycolic acid. Other lactones such as lactide and p-dioxanone and/or their corresponding hydroxy acids can be used. The hydroxy acids can be used, specifically, as chain initiators to control the polyester molecular weight, as determined in terms of their inherent viscosities (I.V.) as approximately 0.1 g/dl solutions in chloroform, and/or to provide chains with a carboxylic end group. The basic nitrogenous polyesters which are the subject of this invention, are to have I.V. of 0.05 to 0.35 dl/g and, preferably, 0.05 to 0.25 and, more preferably 0.10 to 0.20 dl/g.

Two major types of amine functionalities can be introduced into the polyester chain to accelerate its absorption through autocatalyzed hydrolysis. Excluded from the amine-bearing functionalities are bio-active polypeptides. The weight percent of the amine functionalities in the polyesters subject of this invention can be between 1 and 20 and, preferably, 1 to 10. The first type of amine functionality comprises an ionically linked mono- or poly-functional amine which is capable of forming a carboxylate salt with an acid-terminated polyester chain. This can entail, for instance, a caprolactone/glycolide copolymer made using catalytic amounts of stannous octoate and glycolic acid as the chain initiator, and following a typical reaction scheme established for caprolactone polymerization. The resulting acid terminated polyester is then allowed to form carboxylate salts with amine-bearing molecules: lysine, 1-lysine, potassium lysinate, or an alkane diamine as depicted by structures A and B, respectively.

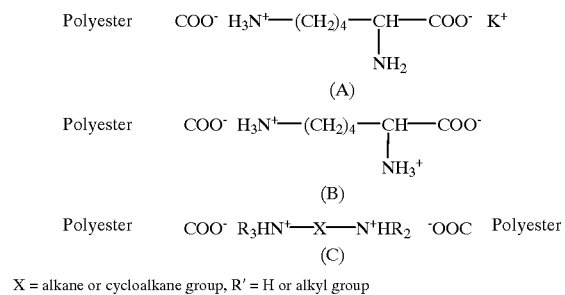

X = alkane or cycloalkane group, R' = H or alkyl group

The second type of amine functionality is covalently incorporated into the polyester chain. This can be achieved by amidation of preformed polyester with di- or polyfunctional amine or using di- or poly-amine with at least one reactive hydrogen as the chain initiator, such as 1-methyl 4-aminomethyl-piperidine and 3,3'-diamino-N-methyl-diproppylamine. The ring opening polymerization can be achieved using catalytic amounts of stannous octoate. Typical polyesters covalently linked to the amine functionalities can be illustrated by structures D and E shown below.

(D)

n=1 or 5
R=$CH_3$ or $C_2H_5$
X=alkane or cycloalkane group

(E)

n=1 or 5
R=$CH_3$ or $C_2H_5$
X=Alkane or cycloalkane group

Although this invention addresses low melting crystalline polyesters made predominantly of ε-caprolactone, those skilled in the art can foresee the use of other aliphatic polyesters as the base materials and incorporate the amine functionality to the acid terminated polyester chains by salt formation or the amidation of pre-formed polyester chains using amino compounds similar to those associated with structures D and E above.

The coating can be applied to the braided suture as a low viscosity melt at temperatures between 70° C. and 100° C. and, preferably 70° C. and 90° C. Excess coating can be removed by passing through a pad of non-woven fabric, e.g., polypropylene or a sizing die. More traditional methods of coating application can entail the use of 1 to 15 percent solution and, preferably, 2 to 10 percent in an organic solvent such as toluene at room temperature or between 25° C. and 50° C. The solvent can then be evaporated by air-drying at room temperature or between 25° C. and 75° C. Other solvents or mixtures of solvents can be used as substitutes for toluene or acetone. The coated suture can be further treated thermally to insure even distribution of the coating on the braid components. Typical sutures which can be coated with compositions subject of this invention include those made of polyglycolide and polyethylene terephthalate. Depending on the suture size, the percent add-on of the coating can be varied between 1 and 10 percent and, preferably, 1.5 to 4.5 percent as the suture decreases from say size #1 to size #6-0. At such level of coating, the suture handling and tie-down characteristics are improved substantially without compromising other properties such as visibility, surface appearance, and knot strength and security.

The absorption profile of the coating is such that it will not affect that of an absorbable suture to any discernable extent. Typically, when representative coatings subject of this invention are used on polyethylene terephthalate sutures incubated in a phosphate buffer at 37° C. and pH of 7.26 lose 50 to 100 percent of their original mass in two to six months.

The following examples illustrate the claimed invention and are in no way intended to limit its scope.

EXAMPLE 1

Synthesis of Acid-terminated Polycaprolactone Polymer A

ε-Caprolactone (57.1 g, 0.5 mole) glycolic acid (7.6 g, 0.1 mole) and stannous octoate (0.5 ml of 0.1 M solution in toluene, 20 mg, $5 \times 10^{-5}$ mole) were added to a glass reactor. The reactor was purged with dry nitrogen gas. The reactor was heated in an oil bath at 180° C., under nitrogen, for 12 hours while the contents were magnetically stirred. The resultant homopolymer has a Tg of –60° C. and Tm of 39° C. as measured by DSC. The resultant polymer inherent viscosity is 0.1 dl/g at 30° C. in hexafluoroisopropyl alcohol.

EXAMPLE 2

Preparation of Potassium L-lysinate Salt of Polymer A

Potassium L-lysinate (1.25 ml of 2.0 M solution in methanol, 25 mmole), is slowly added with stirring to Polymer A (4.4 g) in 100 ml tetrahydrofuran at room temperature. The tetrahydrofuran is then removed by vacuum. The structure of the resultant coating as an onium salt was determined by IR and NMR. The Tg and Tm were shown by DSC to be –62° and 44° C., respectively. Elemental analysis data were consistent with the proposed chemical structure:

|  | % N | % K |
|---|---|---|
| Found | 1.52 | 2.23 |
| Calculated | 1.45 | 2.05 |

EXAMPLE 3

Synthesis of Random Copolymer of 98.5/1.5 Caprolactone-glycolide, Copolymer B

ε-Caprolactone (57.1 g, 0.5 mole), glycolide (1.1 g, 9.5 mmole), glycolic acid (7.6 g, 0.1 mole) and stannous octoate (0.5 ml of 0.1 M solution in toluene, 20 mg, $5 \times 10^{-5}$ mole) were added to a glass reactor. The reactor was purged with dry nitrogen gas. The reactor was heated in an oil bath at 180° C. under nitrogen for 12 hours, while the contents were magnetically stirred. The final composition was determined by $^1$H NMR is shown to be essentially the same as the theoretical. The Tg is –62° C., and the Tm is 37° C.

EXAMPLE 4
Preparation of Potassium L-lysinate Salt of Copolymer B

Potassium L-lysinate (1.25 ml of 2.0 M solution in methanol, 25 mmole), is slowly added with stirring to Polymer B (4.4 g) in 100 ml tetrahydrofuran at room temperature. The tetrahydrofuran is then removed by vacuum. The structure of the resultant coating as an onium salt was determined by IR and NMR. The Tg and Tm were shown by DSC to be −60° and 39° C., respectively. Elemental analysis data were consistent with the proposed chemical structure:

|  | % N | % K |
|---|---|---|
| Found | 1.31 | 2.03 |
| Calculated | 1.45 | 2.05 |

EXAMPLE 5
Synthesis of Random Copolymer of 95/5 ε-caprolactone/glycolide, Copolymer C Following a procedure similar to that used for the synthesis of Copolymer B, copolymer C was made and shown to have an inherent viscosity of 0.1 dl/g in HFIP at 25° C. It has a Tg of −60° C., and Tm of 40° C.

EXAMPLE 6
Preparation of Potassium L-lysinate Salt of Copolymer C

The salt is prepared following a procedure similar to that used for the preparation of the salt of Copolymer B. The composition of the resultant coating was consistent with its elemental analysis and N R data. The Tg and Tm were shown by DSC to be −53° C. and 36° C., respectively.

EXAMPLE 7
Synthesis of Acid-terminated Polycaprolactone, Polymer D

ε-Caprolactone (57.1 g, 0.5 mole) lactic acid (9.0 g. 0.1 mole) and stannous octoate (0.5 ml of 0.1 solution in toluene, 20 mg, 5×10$^{-5}$ mole) were added to a glass reactor. The reactor was purged with dry nitrogen gas. The reactor was heated in an oil bath at 180° C., under nitrogen, for 12 hours, while the contents were magnetically stirred. The resulting Polymer D was removed and shown to have an inherent viscosity of 0.1 dl/g in hexafluoro-isopropyl alcohol.

EXAMPLE 8
Preparation of Amine-trerminated Polycaprolactone, Polymer E

ε-Caprolactone (57.1 g, 0.5 mole), 1-methyl-4-aminomethyl piperidine (2.5 g, 0.02 mole) and stannous octoate (0.5 ml. of 0.1 M solution in toluene, 20 mg, 5×10 mole) were transferred to a predried glass reactor under oxygen-free dry nitrogen atmosphere. The reaction mixture was heated to 170° C. under dry nitrogen. The polymerization was continued for 12 hourd while the contents were magnetically stirred. The resulting Polymer E was removed and shown to have an inherent viscosity of 0.15 dl/g in hexafluoroisopropyl alcohol.

EXAMPLE 9
Preparation of Polycaprolactone with Internally Placed Amine Functionality, Polymer F Using the same polymerization scheme as in Example 8 and all reagents except 1-methyl-4-aminomethyl piperidine, which was replaced by 3,3'-diamino-N-methyldipropylamine (2.32 g, 0.016 mole) to produce a polymer having as inherent viscosity of 0.13 dl/g.

EXAMPLE 10
Preparation of Potassium L-lysinate Salt of Polymer D

This is done following a procedure similar to that used for the preparation of the coating in Example 2.

EXAMPLE 11
Solution Coating of Size 2-0 Polyglycolide Braided Suture

The suture is dipped 5–10 times in a 2 percent solution of the coating (from Examples 2, 4, or 6) in methylene chloride, with each coat dried in between dips. This yields a very thin homogeneous coating layer (typically 2.5 to 5 weight percent of the suture) which gives excellent knot tie-down properties both wet and dry, with no visible flaking.

EXAMPLE 12
Application of Molten Coating Polymer to Size 2-0 Polyglycolide Braided Suture The suture is passed through the molten coating (from Examples 2, 4, or 6) in a temperature of 5° C. to 50° C. above the melting temperature of the coating material, and then threaded through two non-woven Teflon® pads under slight compression to remove excess coating. This yields a thin, uniform coating layer (typically 5 weight percent of the suture). The coated suture exhibited excellent knot tie-down properties both wet and dry, with no visible flaking.

EXAMPLE 13
Absorption Profiles of Coatings

Depending on the composition of the polyester component as in Examples 4 and 6 of the coating, and the level of amino groups, the mass loss ranges from 10 to 20 at three weeks, 40 to 50 at ten weeks, and 55 to 65 at thirteen weeks. To obtain accurate weight loss, a size 2-0 non-absorbable suture braid made of polyethylene terephthalate was used.

EXAMPLE 14
Synthesis of a 95/5 -Caprolactone/glycolide Copolymer(J)

ε-Caprolactone (456.6 g., 4 mole), glycolide (24.4 g, 0.21 mole), glycolic acid (30.4 g, 0.4 mole), and stannous octoate (4 ml. of 0.2 M solution in toluene, 0.8 mmole) were transferred to a predried, stirred reactor. The polymerization charge was treated as follows: (1) after purging with dry argon, the charge was heated to 50° C. under reduced pressure (about 0.1 mm Hg) for 30 min.; (b) the reaction pressure was returned to atmospheric and the polymerization charge was heated to 150° C. while stirring, and kept at this temperature for 14 hours; © the temperature of the polymer was lowered to 120° C. and vacuum was applied for about 35 min. before cooling to 80° C. and bringing the pressure to one atmosphere with argon; and (d) the polymer was transferred to a predried jar for storage at room temperature and reduced pressure. The final composition was determined by NMR and shown to be essentially the same as expected.

EXAMPLE 15
Preparation of L-lysinate Salt of Copolymer G

Copolymer G (5.0 g.) was dissolved in 50 ml. acetone. A soluiton of l-lysinate (0.5 g. in 1.5 ml. water) was added dropwise (5 min) to the copolymer solution under argon atmosphere, while stirring. Upon completing the addition, the solution was stirred further for about 30 min.; then 5 g of anhydrous sodium sulfate were added, and the mixture was stirred at room temperature for at least 4 hours. The mixture was then filtered and the filtrate was transferred for storage under dry argon atmosphere at about 40° C. Part of the filtered solution of the 1-lysine salt was evaporated under reduced pressure at 25° C. and then at 40° C. The infrared spectra of the resulting solid were consistent with the expected structure.

EXAMPLE 16
Solution Coating of Size 2-0 Polyglycolide Braided Suture

The suture was threaded through a 10% acetone solution of the 1-lysine salt of copolymer G. The coated suture was dried at room temperature, and displayed similar characteristics to those described in Example 11.

Similarly, coating solutions for monofilament, multi-filament and braided sutures may be made using 90 to 99% by weight of the acid terminated caprolactone polymer of Example 14 and 1 to 10% by weight 1-arginine following a procedure similar to that used for the preparation of the coating in Example 15. The suture, such as a size 2-0 polyglycolide braided suture, may be coated as described in Example 16.

The polymers of the present invention have other important uses, as absorbable lubricious coatings. As such, these polymers may be used as coatings for surgical staples and other surgical closure devices such as facia fasteners. In addition, the polymers of the present invention may also be used to coat percutaneous surgical devices, such as trocars, endoscopes, and endoscopic catheters, instruments and devices. For the needles of syringes and catheters, and for catheters in general, these polymers may replace silicone and teflon lubricants.

An example of an antibiotic, lubricant coating for a catheter can be made by mixing a 5% acetone solution of the polymer salt of Example 17, at 85 to 90% by weight, with a 20% aqueous solution of cephalexin hydrochloride monohydrate, at 1 to 15% by weight. The mixed system may then dried with anhydrous sodium sulfate and kept at 4° C. in a dark container under dry argon until used. The intravenous catheter may be dipped into the mixed solution for 1 to 20 minutes and air dried in a laminar-flow hood.

In fact, the polymers of the present invention may be used to coat most surgical implants. In this regard, it is to be noted that coatings of the polymers of the invention may incorporate bioactive agents such as growth factors, antimicrobials and antibiotics, especially useful to combat implant-induced infection. In a similar manner, coatings of the polymers of the present invention may be used to coat synthetic vascular grafts and similar graft devices such as stents, and shunts. They may also be used to coat open-cell microporous templates or constructs, such as those made of open-cell sponge, for use in tissue regeneration.

The speed of the hydrolysis of the nitrogenous polyesters of the present invention may be modulated to suit the many uses of the polymer. Polymers with the amine-bearing structures at the chain ends, linked ionically to the polyester sequences, will autocatalyze more slowly than if the amine-bearing structures are covalently linked to the chain ends, as the residence time of the catalytic component of the tonically linked amine structure will be shorter than the residence time of the catalytic component of the covalently linked amine structure. Similarly, if the amine-bearing structure is internally placed, the projected residence time of the catalytic component will be greater, and these nitrogenous polyesters will undergo autohydrolysis faster.

The nitrogenous polyesters of the present invention are pliable and waxy. They may be used to replace bone wax, and, with or without a solvent, may be used as a tissue sealant spray or a compliant barrier. The polymers of the present may also be used to form a matrix for peptides and proteins for use in modulating certain biological events, such as cell division; and as a matrix for vaccines and growth factors. They may also be used as a carrier for viable cells, such as chondrocytes cells for cartilage, and osteoblasts, and/or growth factors, such as insulin, and platelet derived growth factor.

The nitrogenous polyesters of the present invention are also useful as hemostatic agents. In this use, its performance may be augmented by certain metal ions known for hemostatic use, such as multivalent ions of calcium, iron, zinc, chromium and magnesium. The polymers of the present invention may also be put to use as components of therapeutic or prophylactic systems for managing orthopedic, vascular, or dental infection. For example, osteomyelitis.

What is claimed is:

1. A bioabsorbable, lubricant coating for surgical devices comprising surgical staples; facia fasteners trocars, syringes; endoscopes and endoscopic catheters, surgical implants; vascular grafts; shunts; and stents; an open cell, microporous template for tissue regeneration; a matrix for peptides and proteins; a matrix for vaccines and growth factor; and a bioabsorbable carrier for viable cells, said coating comprising crystalline nitrogenous polyesters comprising predominantly $\epsilon$-caprolactone polymer sequences linked ionically or covalently to amine-bearing structures which represent 1 to 20 percent of the total weight.

2. A lubricant coating as in claim 1, further comprising a bioactive agent.

3. A lubricant coating as in claim 2, wherein the bioactive agent is an anti-microbial.

4. A bioabsorbable, lubricant coating for a surgical closure device as in claim 1, wherein the coating comprises a crystalline nitrogenous polyester comprising predominantly $\epsilon$-caprolactone polymer sequences linked ionically or covalently to amine-bearing structures which represent 1 to 20 percent of the total weight, and wherein the polyester chain is terminated with a carboxyl group and wherein the polyester is ionically linked to arginine.

* * * * *